United States Patent [19]
Fisk

[11] Patent Number: 5,882,321
[45] Date of Patent: Mar. 16, 1999

[54] LEG SLING AND ABDOMINAL BELT

[76] Inventor: Mary J. Fisk, 2020 N. Pantops Dr., Charlottesville, Va. 22911

[21] Appl. No.: 922,834

[22] Filed: Aug. 26, 1997

Related U.S. Application Data

[60] Provisional application No. 60/024,447, Aug. 27, 1996 and provisional application No. 60/038,417, Feb. 18, 1997.

[51] Int. Cl. [6] .................................. A61F 5/00; A61F 5/37
[52] U.S. Cl. .................................. 602/4; 602/23; 128/875
[58] Field of Search ............................... 602/4, 5, 12, 19, 602/23, 24; 128/845, 869, 875, 876, 883; 135/66, 68

[56] References Cited

U.S. PATENT DOCUMENTS

| | | | |
|---|---|---|---|
| 4,913,136 | 4/1990 | Chong et al. | 602/24 |
| 5,256,119 | 10/1993 | Tudor | 602/23 X |
| 5,375,279 | 12/1994 | Toso | 602/23 X |
| 5,403,268 | 4/1995 | Clement | 602/4 X |
| 5,542,433 | 8/1996 | Saupe | 128/869 |
| 5,643,184 | 7/1997 | Toso | 602/19 |

*Primary Examiner*—Richard J. Apley
*Assistant Examiner*—Denise Pothier
*Attorney, Agent, or Firm*—Sheldon H. Parker

[57] ABSTRACT

The sling of the instant invention is carried or supported by an abdominal belt, such that the weight of the leg of the user is carried by the hips and/or back of the user. The foot is supported in a portion along the vertical line of the body or forward of the vertical line of the body, relative to the body line when the user is not walking. In use, the person will support the body on the good leg, swing the crutches forward and the move the upper body forward until the body is supported by the crutches. The sling is essentially, a U-shaped member, with the bottom of the U forming a cradle for the foot. The upper ends of the sling, that is, the elongated legs of the U, are attached to the abdominal belt. The attachment mechanism can also consist of looping the free ends of the sling over the abdominal belt and securing the ends of the sling to a midsection or lower section of the sling legs, by fastening means, such as VELCRO brand hook and loop fasteners.

18 Claims, 11 Drawing Sheets

LEG SLING AND ABDOMINAL BELT

This Application claim the benefit of U.S. Provisional Appln. No. 60/024,447, filed Aug. 27, 1996 and Provisional Appln. No. 60/038,417 filed Feb. 18, 1997.

BACKGROUND OF THE INVENTION

1. Field of the Invention

The present invention relates to a sling for use in support of a leg, and more particularly, to a leg support sling which is suspended from an abdominal support belt. The abdominal support belt can be of the type which includes an elongated flat waist band and one or more supplemental elastic tensioning straps which overlie the waist band, and a pair of braces which extend over the shoulders of the user.

2. Brief Description of the Prior Art

While arm slings come in a variety of forms, styles, shapes and uses, leg slings are all but unknown. U.S. Pat. No. 2,543,847, disclosing a leg sling acknowledges that for certain types of unilateral leg diseases, for example the disease known as Legg-Perthes disease, it is extremely important that, during the convalescent period, the ambulatory patient's afflicted leg be freed from bearing any weight. According to the patent, if the leg is not so freed from weight bearing, the disease will be prolonged and the bones of the leg, in particular the femur, will not become properly mended. This lack of proper healing frequently results in a considerable shortening of the afflicted leg. The patent further indicates that plaster casts do not effectively relieve the afflicted leg from weight bearing. The use of crutches, with the patient holding the foot of the afflicted leg off the floor can prove helpful, but notwithstanding all care and conscientiousness on the part of the patient and careful observation by others, the patient will inevitably apply some weight to the afflicted leg. The patent goes on to disclose a sling which eliminates all weight bearing by the afflicted leg, by supporting the leg in a rearwardly directed, elevated position. The sling is used in conjunction with crutches, thereby enabling the user to walk on one leg and two crutches. The sling is formed of an elongated flexible strap of webbing or other suitable material, one loop end of which is around the leg of the user, and the other loop end is over the patient's shoulder. The sling of U.S. Pat. No. 2,543,847 has two major shortcomings. A primary shortcoming is that the pressure on the shoulder is so severe that the user is unable to use the sling for more than minutes, let alone during an entire day. The other problem is that the rearward support of the leg causes the sling to interfere with the chair when the user attempts to sit.

U.S. Pat. No. 5,172,703 discloses a device which is a soft tissue correction aide. According to the patent an assembly (2) provides a length adjustable belt (4) and to which is secured a pair of length adjustable suspenders assembly (6) and a plurality of tensioning strap assemblies (8). In normal use, the belt (4) is fit to the waist of the user and the suspenders (6) are secured about the user's shoulders. Appropriate length adjustments are made to properly fit the belt (4) to the waist and the suspenders (6) to the shoulders.

The '703 patent further states that extending from the belt (4) are individual tension control straps (8). The straps (8) can be affixed at a single or multiple locations along the belt (4) and may either be permanently or removably mounted to the belt (4). For the arrangement shown, the straps (8) extend from the belt (4) and behind the waist and hips of the user to wrap over the forward surfaces of the shins and clip to outside fasteners mounted to a pair of shoes (12) (reference FIGS. 3 and 4). A corresponding external, torsional pressure is thus applied about the legs of the user to induce the feet to point inward and correct for an out-toeing condition. Alternatively, the straps (8) can be trained about the front surfaces of the thighs and attach to inside fasteners (10) provided at each shoe. An internal torsional adjustment is thereby provided to correct for an in-toeing condition. Numerous other strap mountings can be effected as necessary to correct for other soft tissue misalignment. Depending upon the condition, the straps (8) may be secured to different locations of the shoe.

The specific torsional tension is determined from the relative length established for each strap (8) and the elasticity of each strap. Provided the user maintains an erect posture, a substantially constant force induces an opposite, sustained corrective force to realign the related body part to which the ends of the straps (8) are secured. The elasticity of the straps (8) not only accommodate the required torsional correction but also normal body movements of the affected limbs, such as during walking. The assembly (2) may also be worn during sleep.

With attention to FIG. 2 of the '703 patent, the belt (4) particularly comprises a length of a durable and/or corded material, such as heavy canvas, having a web width in the range of two to four inches. The cut ends or edges of the material are hemmed to prevent fraying. Provided along inner and outer mating surfaces of the belt (4) are pieces (16) and (17) of mating hook and loop Velcro fastener material and whereby the length of the belt (4) can be adjusted, depending upon the amount of overlap.

Permanently hemmed along the upper periphery of the belt (4) are the suspenders (6). Secured along each suspender (6) are looped adjusters (18), whereby the suspender length may be tailored to the body trunk. Alternatively, the suspenders (8) may either be deleted from the belt (4) or detachably secured thereto in the fashion of the assembly (34) of FIG. 6.

Anchored at common hem points along the sides of the lower edges of the belt (4) are pairs of tension control straps (8). The mounting position of the straps may be varied as desired relative to the condition to be treated. The straps (8) may also all be hemmed to a common location, such as the center of the belt (4). The straps (8) can also include length adjusters (18) (reference FIGS. 5 and 6) or not (reference FIGS. 1 and 2).

The device of U.S. Pat. No. 5,172,703 does not support the injured leg off of the ground through the use of either the belt or shoulder straps. Accordingly, the device of the '703 patent is not applicable for use with medical problems which require removal of weight bearing from the injured leg.

BRIEF DESCRIPTION OF THE DRAWINGS

The advantages of the instant disclosure will become more apparent when read with the specification and the drawings, wherein.

SUMMARY OF THE INVENTION

Figure 1:
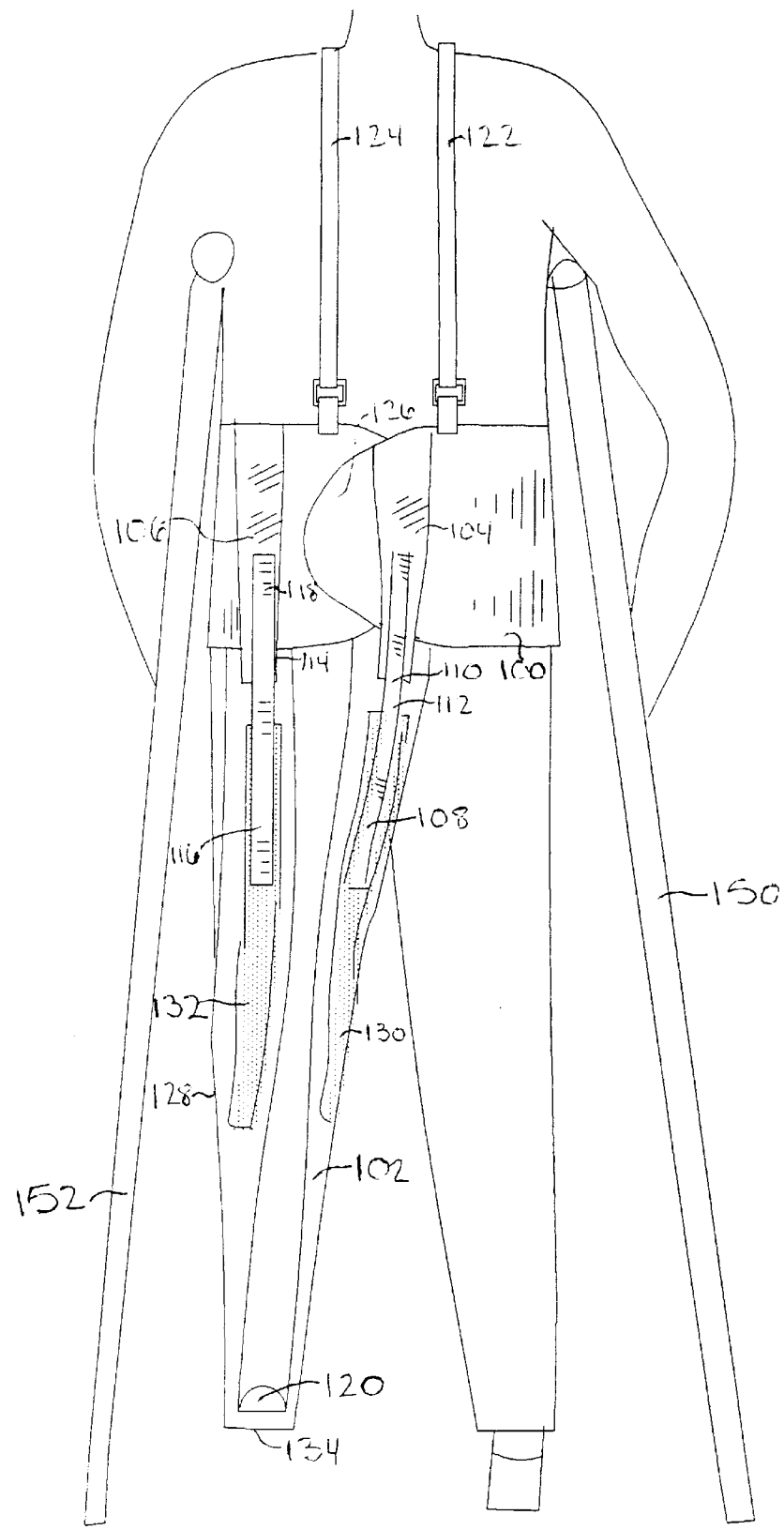
FIG. 1 is a front view of a person with a sling carried by an abdominal belt, and a pair of crutches.

The sling of the instant invention is carried or supported by an abdominal belt, such that weight of the leg of the user is carried by the hips and/or back of the user. The foot is supported in a portion along the vertical line of the body or forward of the vertical line of the body, relative to the body line when the user is not walking. In use, the person will support the body on the good leg, swing the crutches forward and the move the upper body forward until the body is supported by the crutches. The two legs are then swung forward, in unison.

The method of use of the leg support sling of the present invention comprises the supporting a leg of a patient, in coordination with the use of crutches, providing a load bearing structure around the waist of a patient, supporting one leg of said patient in a position which is elevated from the ground when the patient is in a standing position, providing support means beneath the foot of said patient, and maintaining the foot in said elevated position, and carrying the weight of the leg of the patient substantially entirely by the load bearing structure around the waist of said patient.

Additionally, the method involves maintaining the elevated foot in a position, when said patient is in an upright standing position, which is to the rear of the non-supported leg of said patient.

The leg sling structure used to support the weight of the leg of a patient in a bent position, includes the load bearing abdominal waist belt, which is positioned around the waist of a patient. A leg sling is provided which has a first end and a second end. The first end is fixed to the load bearing abdominal belt, such that said load bearing belt is in load bearing relationship with said leg sling. A foot receiving unit is provided at the second end of the sling. A brace, or shoulder harness, is fixed to the load bearing belt and is dimensioned to extend around the shoulders of a patient. The shoulder harness is configured to coordinate with the load bearing means without transferring the weight of the patient's leg from said load bearing means to the shoulder's of the patient.

The leg sling structure includes a sling length adjusting mechanism for adjusting the distance from the first end affixed to the load bearing belt to the foot receiving means at the second end. Thus, the distance from the first end affixed to belt, to the foot receiving section at the second end is shorter that the distance from said load bearing means to the ground, thereby supporting said leg in an elevated position.

The abdominal belt is provided with a mechanism for adjusting the waist width relative to the waist size of said patient, thereby substantially entirely supporting the weight of said leg which is in an elevated position. While the hips of the user can carry great weights, the shoulders of the user, lack such an ability. Accordingly, all of the adjustment mechanisms coordinate to maintain the leg supported by the belt, rather than by the braces.

The leg sling structure can further include a quick sling release mechanism. The quick release is positioned between the leg sling first end and the load bearing belt, such that the user can remove the supported leg from said leg sling foot support at the second end, without altering the mechanism for adjusting the distance from the sling first end to the sling second end. The sling release means can be a hook and loop connector or a buckle. Additionally, a combination of a loop on the belt and a hook and loop connector on the sling means, can be used. The hook and loop connector can be an elongated member which passes through the loop on the belt.

Thus, the sling is essentially, a U-shaped member, with the bottom of the U forming a cradle for the foot. The upper ends of the sling, that is, the elongated legs of the U, are attached to the abdominal belt. The attachment mechanism can also consist of looping the free ends of the sling over the abdominal belt and securing the ends of the sling to a midsection or lower section of the sling legs, by fastening means, such as VELCRO brand hook and loop fasteners.

DETAILED DESCRIPTION OF THE INVENTION

The sling of the instant invention is supported from an abdominal support belt around the waist of the user. The support belt can be of any type as well known in the art. The body 100 can be the same as that described in U.S. Pat. Nos. 5,257,419, 5,176,131, 4,171,555 or 5,500,959 the disclosures of which are hereby incorporated by reference, as though recited in full, or it may be of any other suitable construction.

Figures 3, 4, 5, 6:
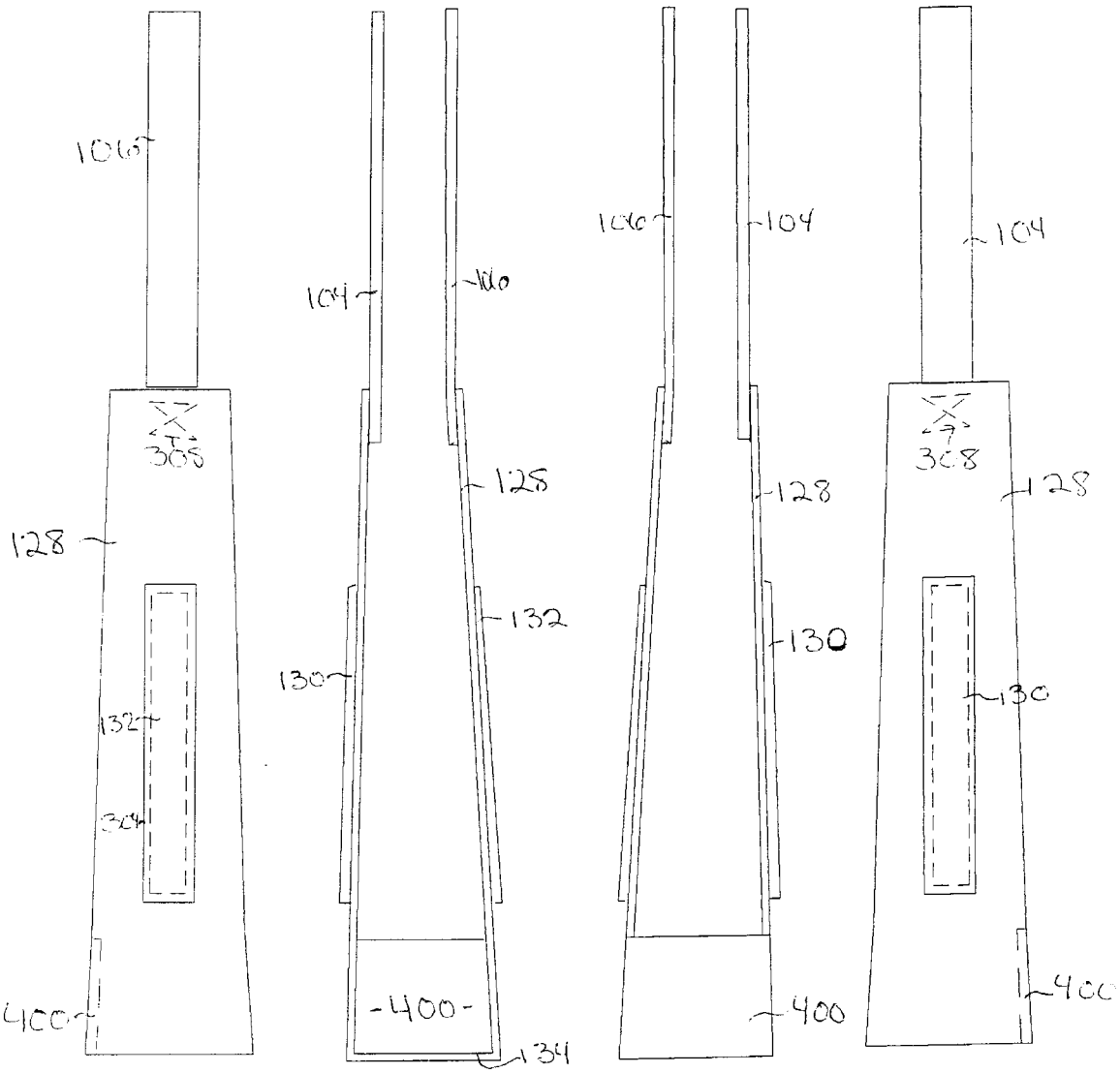
FIG. 3 is a side elevation view of the sling of the present invention.
FIG. 4 is a front elevation view of the sling of the present invention.
FIG. 5 is a rear side elevation view of the sling of the present invention.
FIG. 6 is the alternate side elevation view of the sling of the present invention.

As shown in FIG. 1 of U.S. Pat. No. 5,257,419, the belt 10 is positioned around the abdomen of a user prior to use of the sling of the instant invention. The '419, discloses that to install the belt, the user positions the belt 10 around the waist such that the waist band 12 is adjacent to the waist and the outer section of each tensioning strap 14 and 15 faces outwardly. The end section 20 of the waist band 12 is then positioned against the waist in the vicinity of the navel of the user such that the back surface 28 of the end section 20 is against and facing the waist and the front surface 26 of the end section 20 faces away from the waist. The end section 22 is then placed at least partially over the end section 20 such that hook material of the tip section 36 of the end section 22 engages the loop material of the front surface 26 of the end section 20 to secure the band 12 around the waist of the user. Optionally, a pair of braces 60 formed of a woven elastic material may be provided and positioned around the shoulders of the user to help maintain the relationship between the band 12 and the waist. As can be seen in FIG. 6, the handles 55 and 56 project outwardly from the waist band and are easily reached by the user when the waist band 12 is secured around the waist and the straps 14 and 15 are "relaxed".

To select the desired degree of support of the abdominal belt of U.S. Pat. No. 5,257,419, the user grasps the handles 55 and 56 and forces the handles towards one another in the direction of the abdominal midline of the user to tension the straps 14 and 15. When the desired amount of tension is effected, the engagement surface 58 of the handle 55 is preferably secured to the loop material of the front surface 26 of the end section 20 and the engagement surface 59 of the handle 56 is preferably secured to the loop material of the front surface 30 of the end section 22.

It should be understood that the sling of the instant invention can be used with any design of abdominal belt and the foregoing description is representative of an abdominal belt. The specifics of the belt are of value and importance as defined in the aforenoted representative patents, but is not narrowly critical in the instant invention.

Figure 1R:
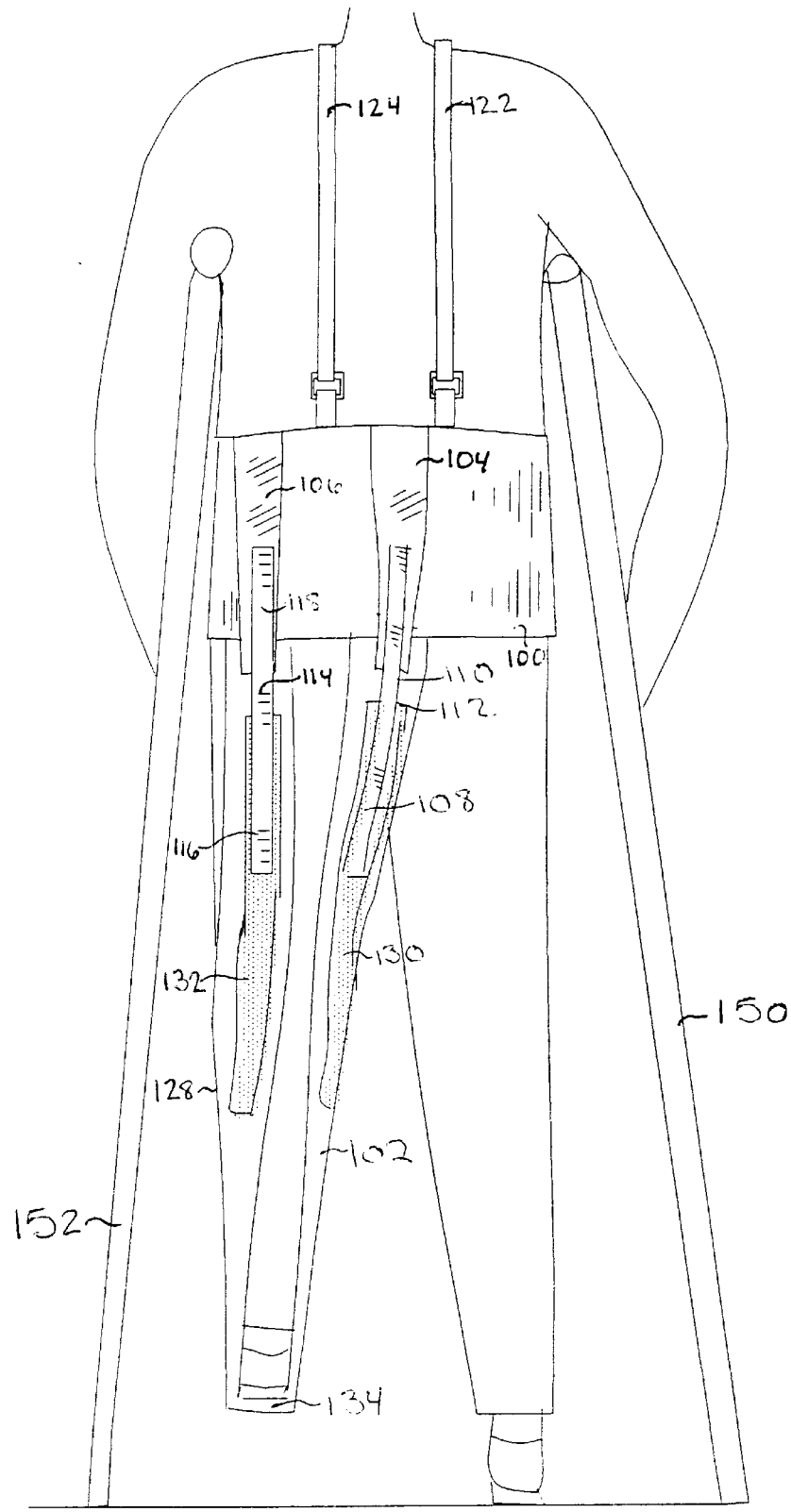
FIG. 1R is a rear view of the embodiment of FIG. 1.
Figure 2:
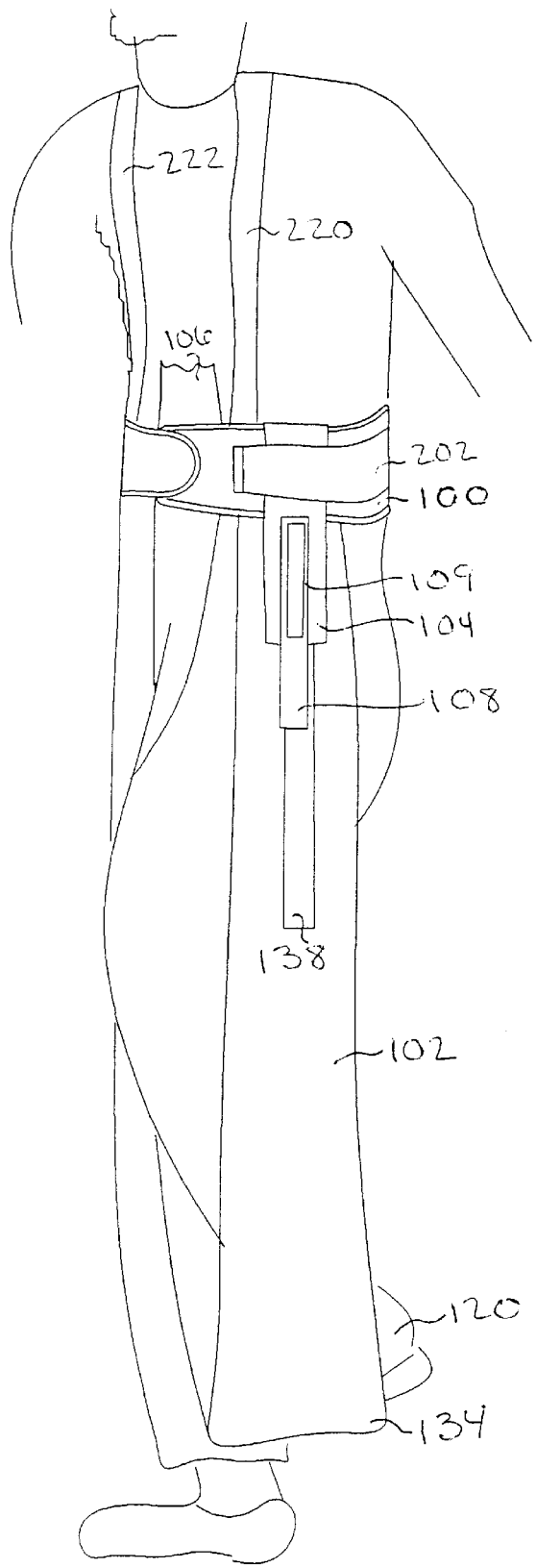
FIG. 2, is a partially side view of a person with the sling of the instant invention.

Looking now to FIG. 1 and FIG. 1R of the instant disclosure, it is seen that the sling of the instant invention includes a sling 128 which is suspended from, or carried by, the abdominal belt 100. The belt can include a pair of braces 122 and 124 which extend over the users shoulders to the rear of the belt 100. One end 126 of the belt 100 is fixed to the underlying opposing end of the belt 126 by any convenient mechanism well known in the art, as for example, hook and loop fasteners, such as sold under the trademark VELCRO®. The sling 128 is essentially a "U" shaped member with the free ends 104 and 106 of the sling 128 looped over the abdominal belt 100. The free end 104 is secured to the main body of the elongated section 102 of the sling by means of hook and loop fasteners. The strap 112 is preferably manufactured from the hook portion of hook and loop material and is sewn to the sling end 104 at the region 110. The hooks of free, lower end 108, engage a region of the cooperating loop fastener 130 which is secured to the elongated section 102. While the hook and loop members can be reversed, it is preferable to have the region 110 of the sling 128 carry the loops and the strap 112 carry the hooks, since the surface of the hooks can be irritating to touch. In the combination as shown, the hooks are conveniently between the sling 128 and the strap 112. Similarly, the other leg of the sling has a free end 106 to which is secured a strap 114. The strap region 118, is secured to the sling end 106 and the hook carrying region end 116 engages the loops of the loop member 132. As shown in FIG. 2, the lower end 134, of the sling 128 supports the foot 120 of the user. Typically, the leg of the user is in a cast, and the foot 120 can be comfortably carried by the sling, whether or not the user is able to wear a shoe.

It is thus evident that the sling can be conveniently used with people of different heights, due to the fact that the hook and loop fasteners are not confined to particular relative positions to provide a locking engagement. With a short user, the strap's ends 108 and 116 of the straps 112 and 114 engage the lower section of the loop fasteners 130 and 132, whereas in the case of a tall user, the ends 108 and 116 engage the upper end of the loops fasteners, as illustrated in FIG. 1.

The sling is conveniently used with crutches which can be of any design, as well known in the art. The sling can be seen to conform to the leg and does not interfere with the use of the crutches 150 and 152.

FIG. 2 shows the sling, in combination with an alternate belt embodiment, supporting the left leg of the user. The free end 106 of the sling is shown cutaway and unfolded to reveal a portion of the abdominal belt 200. The abdominal belt 200 is shown with an elastic member 202 overlying the sling end 104. It should be understood that it is not narrowly critical whether the elastic member 202 is over or under the sling, although the overlying position is preferred, since in this position, the elastic member 202 can more readily be adjusted, as known in the art.

One end of the strap 108 is shown sewn, along line 109 to the end 104 of the sling. The sling most conveniently is made of a flexible but substantially inelastic fabric such as canvas, polyester, polypropylene or other natural or synthetic material. The material can be woven fabric or a sheet material.

As seen in FIGS. 3 through 6, the loop carrying member 132 is sewn to the sling 128 along stitch line 304. The upper strap 106 is similarly sewn to the sling 128 along stitch line 308. As seen in FIG. 4, the flat bottom support region 134 is attached to a stop member or support 400. The toes of the user normally rest against the stop member 400, thereby keeping the foot of the user in place. The usual movement of the leg would tend to force the foot into the sling in the direction of the stop member 400. Alternatively, the stop can be against the heel of the user, if the user prefers, or has a tendency to move the leg backward out of the sling. The bottom region 134 and side portions of the sling are sewn to the end member, or otherwise conveniently secured together. The stop 400 can be a flap region which is an extension of the bottom region 134. As evident from FIGS. 3, 4, 5, and 6, the sling is symmetrical.

The combination of the sling 128, and the abdominal belt 100, enables the user to support the leg in the off the ground position, by incorporating use of the back muscles. This is in contrast with the sling of U.S. Pat. No. 2,543,847, in which the entire weight is carried by one shoulder of the user. It was found that the use of the sling 128 in the manner of U.S. Pat. No. 2,543,847, produced discomfort which was so severe that the sling had to be removed after about five minutes. By way of contrast, when the sling was supported by the abdominal belt, it can be used comfortably for extended periods of time and does not impede travel, as for example, in a car and an airplane. Additionally, supporting the leg in the forward position, as illustrated in FIG. 2, is far more comfortable than when the leg is supported rearwardly, as in the '847 patent. By rearward support, is meant that the foot is well behind the vertical line of the body. In accordance with the preferred embodiment of the instant invention, the foot of the user is approximately positioned along the vertical line of the body or preferably, slightly forward of the vertical line. In some circumstances, however, it may be required that the leg be supported in the rearward position. In these instances, the user need only position the upper ends 106 and 104 of the sling at the location along the belt which provides the required foot support position. For example, FIG. 2 shows the sling end 106 between the shoulder straps 220 and 222. It can be advantageous to position the slings such that the end 106 is in the location shown for end 104, in FIG. 2, and the end 104 is positioned further to the side to provide room for the end 106. Thus, both sling ends are positioned along the side of the belt 200.

Figure 8:
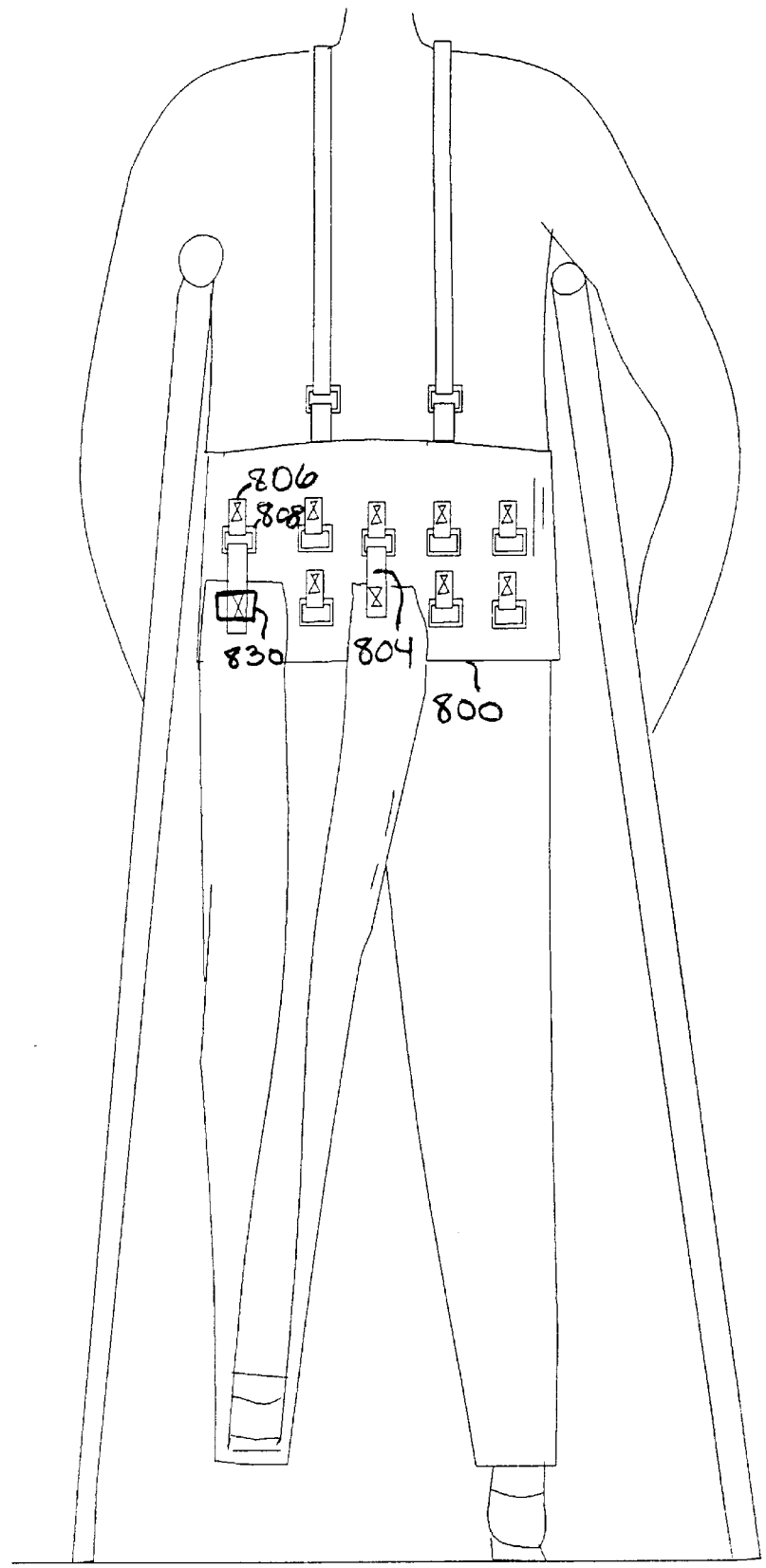
FIG. 8 is a rear view of a user with a belt having a plurality of attachment members and showing a sling attached to two attachment members.
Figure 12:
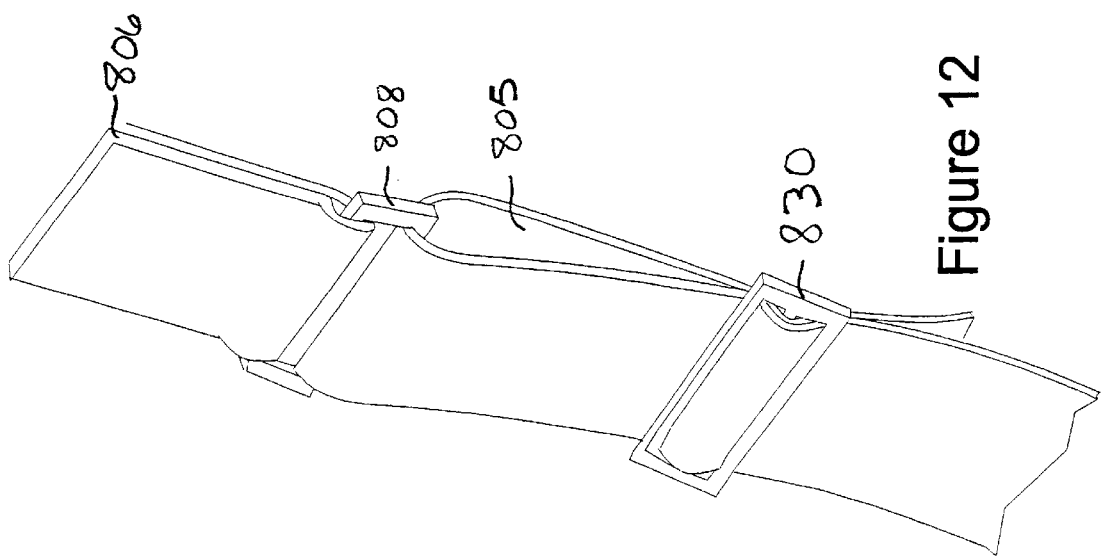
FIG. 12 is a perspective view of a strap adjustment member.

As shown in FIG. 8, the sling can be attached to the abdominal belt 800 by means of straps 804 and 805. The straps 804 and 804 and 805 can be secured to the belt 800 by looping the straps 805 through the loops 808 and secured to itself through use of securing loop 830. This arrangement as illustrated in detail in FIG. 12. A number of loop strap 806 and loop 808 combinations can be included along the belt 800 to provide for adjustability.

Alternatively, other systems as well known in the art can be used. As for example, U.S. Pat. No. 4,171,555 discloses a buckle device which can readily be employed to provide ease of attaching and removing the sling from the abdominal belt. The disclosure of U.S. Pat. No. 4,171,555 is incorporated herein, by reference, as though recited in full.

The patent discloses that a plastic buckle is adapted to adjustably secure extremities of a web-like material. The '555 buckle includes a frame-like body portion which is secured at one end to the web-like material. The opposing end is dimensioned to receive the second part of the buckle, which is, in turn secured to a free end of the web-like material. At least one of the material to buckle connections provides for adjusting the extremity of the material. This connection includes at least two transverse parallel bars positioned adjacent the opposite end of the body portion.

In order to incorporate an alternate method of attachment, the loop 808 and strap 806, would be replaced with the receiving end of the attachment device and the strap 805 of the sling would be provided with the coordinating end.

Figure 7:
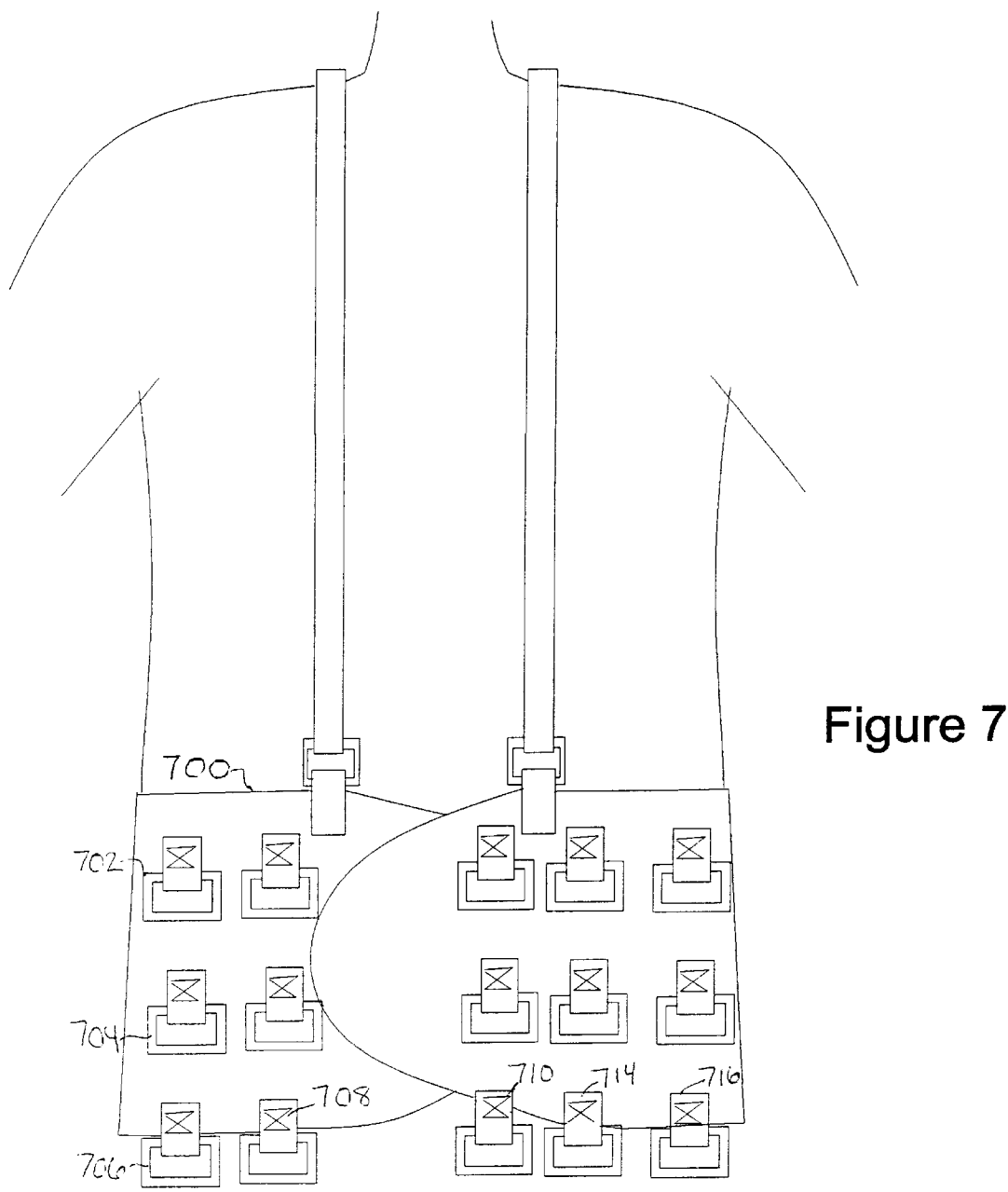
FIG. 7 is a partial front view of a user with an abdominal belt having a plurality of attachment members.

To allow for further adjustment, the belt 700 can be provided with a plurality of loop/strap combinations 702, 704, 706, 708, 710, 714 and 716, as shown in FIG. 7. The belt 700 provides a further example of the possible combinations which can be incorporated in the instant invention. The straps 804 and 805 are secured to any two loops, as previously described.

Figure 9:
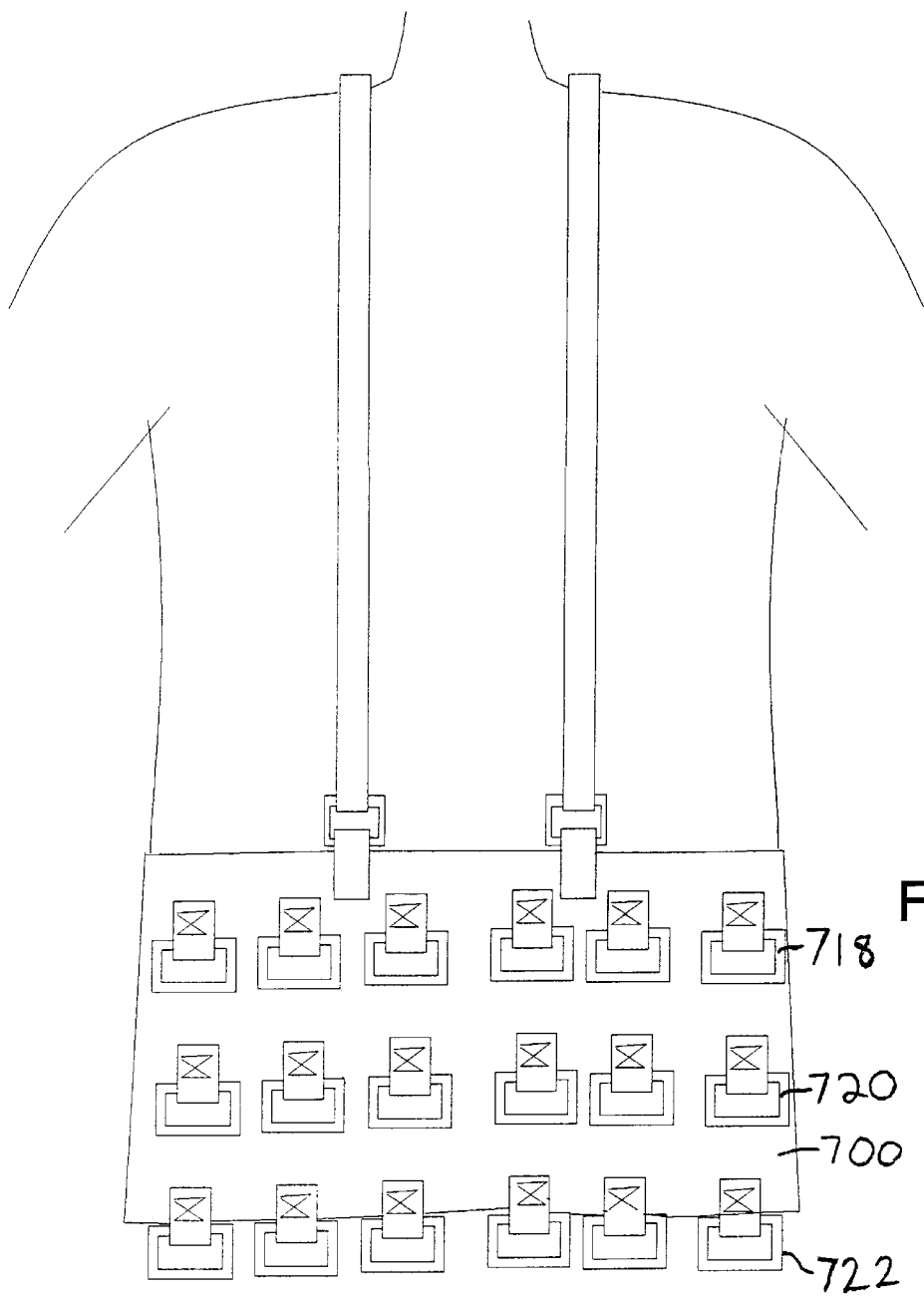
FIG. 9 is a fragmentary rear view of user with a belt having a plurality of attachment members.

The use of loops 702, 704 and 706, at different heights along the belt 700, enables the user to find the most comfortable attachment position. While abdominal belts have corset stays built in to them, and therefore are not prone to curling over, attachment of the straps to the lower end of the belt, at attachment loop 706, can be advantageous to avoid any tendency of the belt to curl. The adjustability of the straps 804 and 805, in combination with the adjustability of the straps 104 and 106, minimizes the need for the use of loops 702, 704 and 706 at different heights along the belt 700, however, availability of different positions along the belt 700, as for example provided by loops, 706, 708, 710, 714 and 716, provides important adjustability. Similarly, as shown in FIG. 9, attachment of the sling at the rear of the belt 700, can be accomplished through the use of attachment loops 718, 720 and 722, at varying locations along the belt and at different heights.

While loops are illustrated for the attachment of the sling, as stated heretofore any attachment device can be used, as well known in the art. For example, the attachment connection device can be a hook and loop, button or snaps. The loops are preferred, because of the ease of providing length adjustments. While in all cases, the leg will be supported off of the ground, accommodation is required due to the different heights of users and different requirements for amount which the foot must be off of the ground. Thus, in all cases, the distance from the abdominal belt to the bottom of the sling will be less than the distance from the bottom of the belt to the ground, the amount of difference will vary, according to the requirements of the user.

Figures 10, 11:
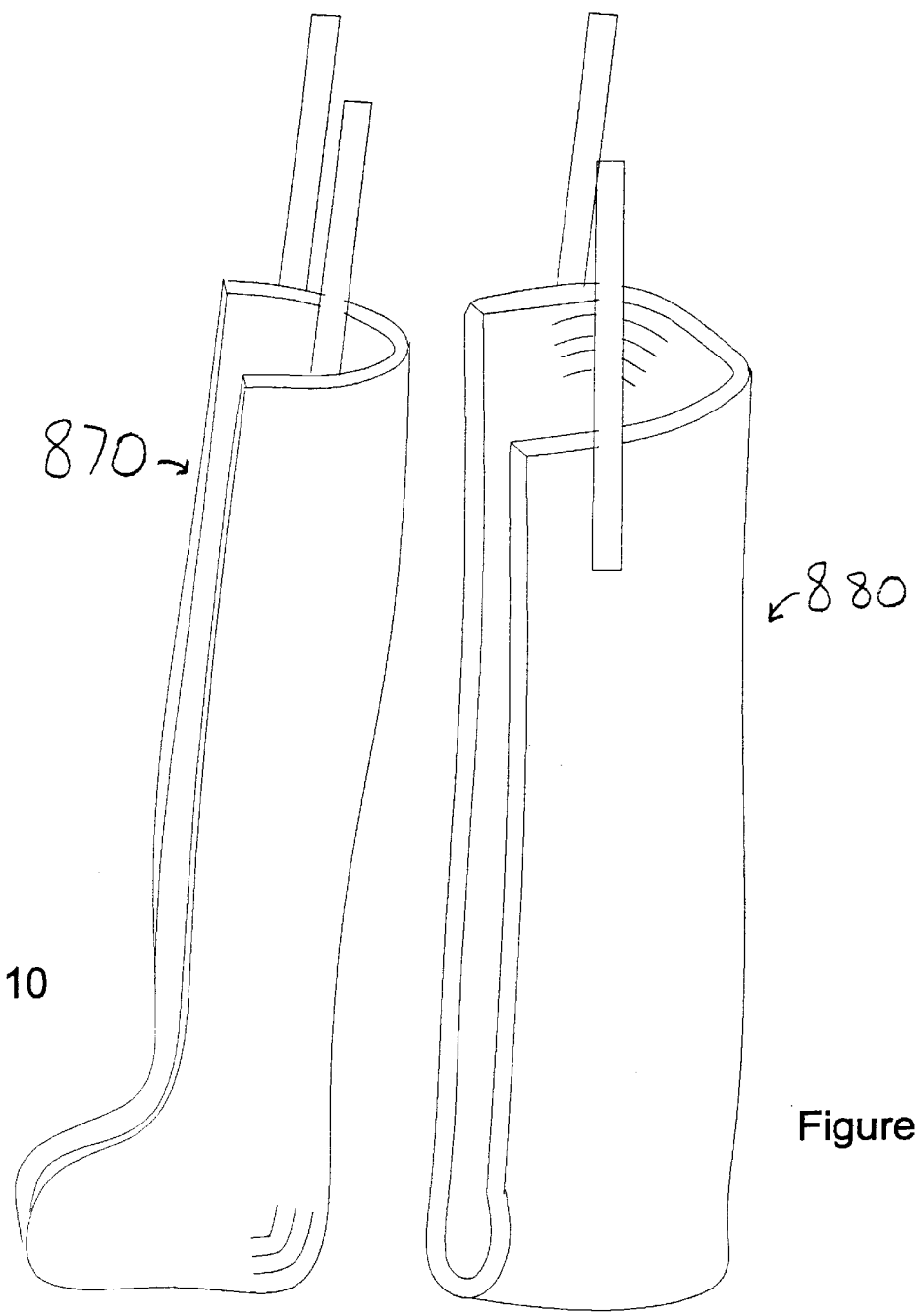
FIG. 10 is an elevation view of an alternate style sling.
FIG. 11 is an elevation view of another alternate style sling.

FIGS. 10 and 11 illustrate additional designs for slings. In each modification, the sling is essentially "U"-shaped in horizontal cross section, thus partially enclosing the leg. The bottom of the sling 870 can conform to the shape of the foot as in FIG. 10, or the sling 880 can be of essentially consistent dimensions along its length, as illustrated in FIG. 11. The slings can be provided with straps to close the open end, thus, the leg would be held within the sling. The straps would keep the sling in place when the user sits, moves into or out of an automobile, or otherwise is not walking or standing. Additional straps can be provided which would enable the user or a person assisting the user, to lift the leg and cast when the user is maneuvering through some awkward position, as for example, into or out of the back seat of an automobile. The straps can have one free end sewn to the sling and the other end releasably attached by VELCRO or other type of connector. The user or assistant can detach the free end of the strap and by gripping the free end, lift the leg from one position to another.

Figure 13:
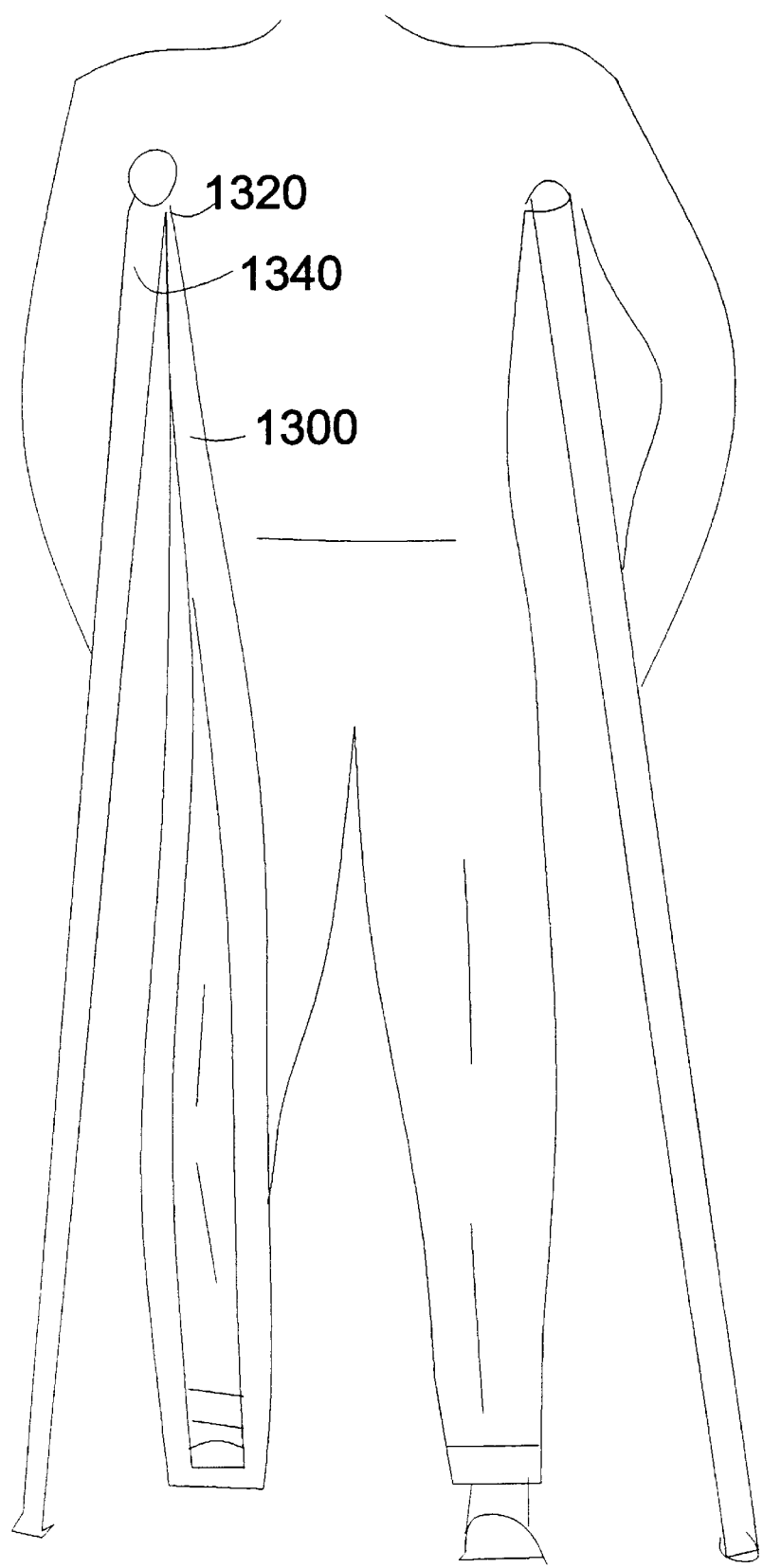
FIG. 13 is an alternative embodiment showing the sling carried by the crutch.

In another modification, as shown in FIG. 13, the sling 1300 can be secured to the crutch 1340 at the upper point 1320, rather than carried by the belt. In this format, the leg need not move directly with the sling 1300, particularly if the sling 1300 is fixed to the crutch at or near the upper, padded end of the crutch 1340. The full weight of the leg and cast are carried by the crutch 1340, thus providing an advantage over the belt design. However, the leg will swing from the movement of the crutch 1340 and will not be as natural a motion as where the leg is supported by the belt.

Figure 14:
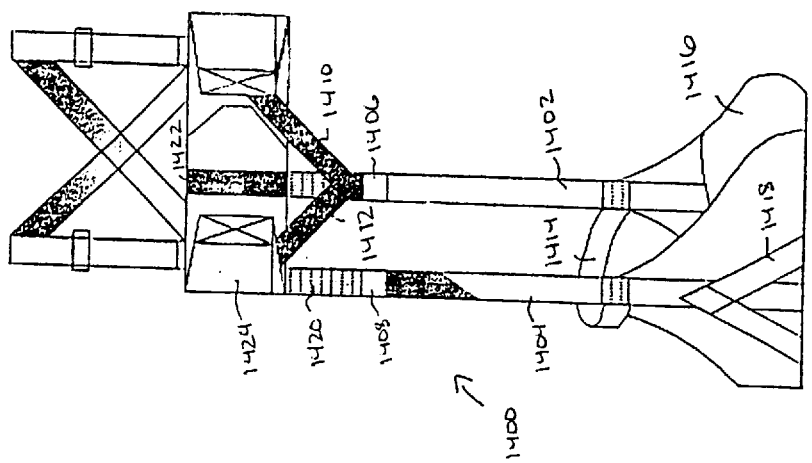
FIG. 14 is a perspective view of an alternate embodiment of the leg sling.

An alternate embodiment is illustrated in FIG. 14 wherein the sling 1400 consists of straps 1402 and 1404 which are provided with buckles 1406 and 1408 at the ends. Stabilizing straps 1410 and 1412 can be used to stabilize the straps 1402 and/or 1404 relative to the abdominal belt. The stabilizing straps 1410 and 1412 can be provided with hook and loop surfaces so as cooperate with the contacted surfaces of the straps and belt. The straps 1402 and 1404 are connected to the sling boot 1416 and can be either a single strip or two strips attached at the bottom of the sling boot 1416. The straps 1402 and 1404 can be manufactured from either a standard material used for slings, or the wool, or loop, portion of a two part hook and wool material. To prevent the user's weight from being centered along one area, reinforcing strips 1418 are provided on the sling boot 1416. The reinforcing strips 1418 are attached to the straps 1402 and 1404 and form inverted "V's" to even out the pressure applied to the sling boot 1416. An adjustable calf strap 1414 is positioned along the straps 1402 and 1404. The calf strap 1414 should provide adjustability along its own length to allow the calf strap 1414 to accommodate different calf widths. The calf strap 1414 can, dependent upon manufacturing preference, be adjusted along the length of the straps 1402 and 1404. The calf strap 1414 can be manufactured from a hook and loop fabric and adjustable to itself or have a metal buckle which allows for the tightening or loosening of the strap 1414. Alternatively, if the straps 1402 and 1404 are manufactured from wool, the calf strap 1414 can have hook fabric at its ends and adjust by direct application to the straps 1402 and 1404.

Figure 15:
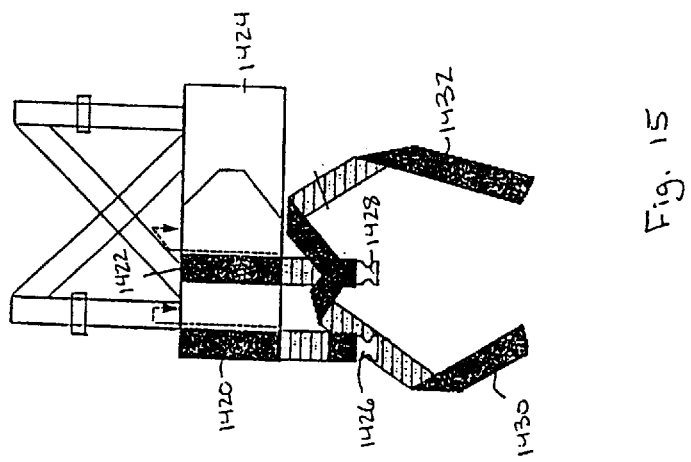
FIG. 15 is a front view of the attachment straps for use with the leg sling of FIG. 14.

A pair of fasteners 1420 and 1422, more clearly illustrated in FIG. 15, are preferably manufactured from the hook and wool material to allow for length adjustability over the belt 1424. One end of the fasteners 1420 and 1422 are provided with buckles 1426 and 1428 which are manufactured to interact with the buckles 1406 and 1408 attached to the straps 1402 and 1404 respectively. Use of the buckles 1408, 1426, 1406 and 1428 allows for the sling straps 1404 and 1402 to be adjusted upon initially wearing the sling 1400. Subsequently, the sling straps 1404 and 1402 can be removed from the fasteners 1420 and 1422 through use of the buckles 1408, 1426 and 1406 and 1428. This eliminates the need to readjust the sling each time it is worn. As an alternative to using hook and wool material for the fasteners 1420 and 1422, a standard fabric can be used and the adjustability obtained at the buckle 1408 and 1406 connection.

In order to provide further stability fastener straps 1430 and 1432 are affixed to one of the braces, in the illustrated embodiment fastener 1422 is used. The fastener straps 1430 and 1432 are manufactured from the hook portion of the hook and wool and will attach themselves to the wool portion of the belt 1424. The use of fastener straps 1430 and 1432 help prevent the sling boot from swinging as well as provide additional securing of the sling strap 1402 to the belt 1424. Although only one pair of fastener straps is illustrated, a second pair can be provided if so desired.

Figure 16:
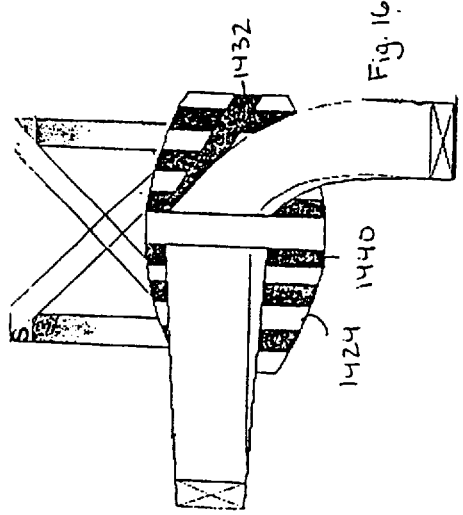
FIG. 16 is a front view of the attachment of the fastener straps of the leg sling of FIG. 14.

In FIG. 16, the belt 1424 is provided with strips 1440 of wool fabric rather than a complete covering of the material. This cuts the cost of manufacture while providing a sufficient adhering area for the hook material used in the fastener 1432.

In order to use the sling illustrated in FIG. 14, 15 and 16, the user adjusts the shoulder straps to the appropriate position and places the sling onto the body. The outer belt is released and allowed to fall away from the inner belt 1424. The side fastener 1420 is applied to the inner belt 1424 and doubled over so that the buckle 1426 is suspended from the inside of the belt at the outer thigh. The front fastener 1422 is then placed over the belt 1424 and doubled over so that the buckle 1428 is suspended from the inner thigh. The fastener straps 1430 and 1432 are applied to the strips 1440 of the inner belt 1424 at the appropriate distance. The outer belt is applied over the inner belt 1424 and secured. The involved foot is placed in the sling boot 1416 and the buckles 1408 and 1406 secured. The sling straps 1402 and 1404 are then adjusted to the appropriate height. The calf strap 1414 is finally adjusted to the appropriate fit.

Additionally, the sling can be provided with pockets to accommodate items which can not be conveniently stored in the clothes of the user.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed is:

1. The method of supporting a leg of a patient using crutches, using a sling device having load bearing means positioned around the waist of a patient, leg sling means, said leg sling means having a first end and a second end, and being affixed at said first end to said load bearing means and having foot receiving means at said second end, said foot receiving means contacting the patient's sole area, such that said load bearing means is in load bearing relationship with said leg sling means, comprising the steps of:

placing said load bearing means around the patient's waist, adjusting said load bearing means to fit the patient's waist, adjusting said leg sling means to a length which elevates the patient's foot from a ground level when standing, placing the sole of the patient's foot to come in contact with said foot receiving means, whereby the patient's foot is supported in an elevated position within said sling means, the weight of the patient's foot and leg being supported by said load bearing means.

2. The method of claim 1, further comprising the step of maintaining the elevated foot in a position, when the patient is in an upright standing position, which is to the rear of the non-supported leg of the patient.

3. The method of claim 1, further comprising the step of affixing said load bearing structure to a harness which extends over the shoulders of the patient, and maintains said load bearing structure around the waist of the patient in a stable position, substantially without transferring the load bearing from said load bearing structure to said harness.

4. A leg sling structure for use in supporting the weight of a patient's leg in a bent position, comprising;

load bearing means, said load bearing means having a first end, a second end and a length and being dimensioned for being positioned around the waist of the patient, leg sling means being substantially inelastic and, said leg sling means having a pair of first ends and a second end and a length there between, said pair of first ends being affixed to said load bearing means and said second end having foot receiving means, said foot receiving means adapted to contact the patient's foot sole area, whereby said leg sling means maintains the patient's foot in an elevated position and the patient's leg in a bent position, the patient's foot and leg weight being born by said load bearing means in load bearing relationship with said leg sling means.

5. The leg sling structure of claim 4, further comprising a shoulder harness, said shoulder harness being affixed to said load bearing means and being dimensioned to extend around the shoulders of the patient, said shoulder harness being configured to coordinate with said load bearing means without transferring the weight of the patient's leg from said load bearing means to the patient's shoulders.

6. The leg sling structure of claim 4, further comprising waist width adjusting means, said waist width adjusting means including means to adjust said length of said load bearing means relative to the patient's waist size.

7. The leg sling structure of claim 4, further comprising at least one sling length adjusting means, said at least one sling length adjusting means being affixed to at least one of said pair of first ends and including means to adjust the distance from said load bearing means to said foot receiving means, whereby said distance from said load bearing means to said foot receiving means is less than the distance from said load bearing means to the ground, thereby supporting the patient's foot in an elevated position.

8. The leg sling structure of claim 7, further comprising at least one sling release means, said at least one sling release means being positioned between said at least one of said pair of first ends and said load bearing means, such that the patient can remove said leg sling from said load bearing means without altering the distance from said at least one of said pair of first ends to said leg sling means second end.

9. The leg sling structure of claim 8, wherein said sling release means have a first portion and a second portion, said first portion being affixed to said load bearing means and said second portion being affixed to said pair of first ends.

10. The leg sling structure of claim 9 further comprising multiple first portion release means placed along said load bearing structure, wherein affixing said second portion release means to two of said multiple first portion release means adjusts the position the support leg rearward of the unsupported leg, when the patient is in an upright, standing position with one leg on the ground, and one leg supported in a bent position.

11. The leg sling structure of claim 9, wherein said sling release means is a hook and loop connector.

12. The leg sling structure of claim 9, wherein said each of said at least one sling release means is a combination of a receiving loop means affixed to said load bearing member, and a hook and loop connector on said first end said sling means, said hook and loop connector being an elongated member, a first end of which passes through said receiving loop and affixes to a second end affixed to said sling means.

13. The leg sling structure of claim 9, wherein said sling release means is a buckle connector.

14. The leg sling structure of claim 4, wherein said leg sling means is an elongated "U" shaped member, said "U" shaped member's pair of open ends forming said pair of first ends, wherein each of said pair of open ends is fixed to said load bearing means.

15. The leg sling structure of claim 14, wherein a first of said pair of open ends is adjustably positioned along the length of said load bearing means.

16. The leg sling structure of claim 14, wherein a second of said pair of open ends is adjustably positioned along the length of said load bearing means.

17. The leg sling structure of claim 4 wherein said sling means second end includes a sling boot adapted for retaining the sole of the foot of the patient.

18. The leg sling structure of claim 17, further comprising at least one front fastener strap means, each of said at least one fastener strap means having a first means and a second means, said first means being affixed to at least one of said pair of first ends and said second means affixed to said sling means length, whereby said pair of first ends are looped over said load bearing means and said first means secured by said second means to maintain the foot in an elevated position, said pair of ends being positioned at a plurality of positions along said load bearing means, such that the supported leg can be positioned rearward of the unsupported leg, when the patient is in an upright, standing position with one leg on the ground, and one leg supported in a bent position.

* * * * *